United States Patent
Sakamoto et al.

(10) Patent No.: US 6,649,028 B2
(45) Date of Patent: Nov. 18, 2003

(54) COLUMN TREATING PROCESS AND APPARATUS THEREOF

(75) Inventors: Kazuhiko Sakamoto, Himeji (JP); Sei Nakahara, Himeji (JP); Masatoshi Ueoka, Himeji (JP); Naoto Kasaya, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/226,013

(22) Filed: Aug. 22, 2002

(65) Prior Publication Data

US 2002/0189927 A1 Dec. 19, 2002

Related U.S. Application Data

(62) Division of application No. 09/696,460, filed on Oct. 25, 2000, now abandoned.

(30) Foreign Application Priority Data

Nov. 8, 1999 (JP) .............................. 11-317547

(51) Int. Cl.[7] .............................. B01D 3/02; C07C 51/44
(52) U.S. Cl. .............................. 203/98; 203/8; 203/100; 203/DIG. 9; 203/DIG. 25; 159/901; 562/600
(58) Field of Search .............................. 203/8, DIG. 21, 203/98, DIG. 25, 100, DIG. 9; 562/600; 210/295; 202/200, 152; 159/901

(56) References Cited

U.S. PATENT DOCUMENTS

| 3,634,200 | A | 1/1972 | Obrecht et al. | |
|---|---|---|---|---|
| 3,891,496 | A | 6/1975 | Erwin | |
| 3,893,893 | A | 7/1975 | Miserlis et al. | |
| 4,021,310 | A | 5/1977 | Shimizu et al. | |
| 4,034,005 | A | 7/1977 | Hancock, II et al. | |
| 4,566,947 | A | 1/1986 | Tsuruta | |
| 5,019,219 | A | 5/1991 | Hamer et al. | |
| 5,207,874 | A | * 5/1993 | Hess et al. | 203/8 |
| 5,330,624 | A | 7/1994 | Ebert | |
| 5,356,520 | A | * 10/1994 | McCarthy et al. | 203/81 |
| 5,637,222 | A | 6/1997 | Herbst et al. | |
| 5,849,161 | A | * 12/1998 | Kishimoto et al. | 203/96 |
| 5,897,749 | A | 4/1999 | Kroker et al. | |
| 6,355,145 | B1 | * 3/2002 | Kresnyak et al. | 203/1 |

FOREIGN PATENT DOCUMENTS

| EP | 0 460 917 A2 | 12/1991 |
|---|---|---|
| EP | 0 561 730 A1 | 9/1993 |
| GB | 788212 | 12/1957 |
| JP | 52-34606 B | 9/1977 |
| JP | 57-61015 B2 | 12/1982 |
| JP | 2-43903 A | 2/1990 |
| JP | 8-239341 A | 9/1996 |
| WO | WO 98/31445 | 7/1998 |

* cited by examiner

Primary Examiner—Virginia Manoharan
(74) Attorney, Agent, or Firm—Haugen Law Firm PLLP

(57) ABSTRACT

The present invention provides a column treating method by use of a distillation column and so on, which method enables to effectively remove solid impurities such as precipitates and polymers contained or produced in a treating fluid, and to thereby stably operate the column treatment. Solid impurities in a treating fluid can be removed by carrying out: step (a) of drawing out the treating fluid from a drawing out outlet (16) at the column bottom of the treatment column (10) outside the treatment column (10), step (b) of removing solid impurities from the treating fluid, drawn out in step (a), by a strainer (40), and step (c) of returning the treating fluid, from which the solid impurities are removed in step (b), to a returning inlet (18) of the treatment column, with advancing physical and/or chemical treatment of the treating fluid in the treatment column (10).

2 Claims, 2 Drawing Sheets

COLUMN TREATING PROCESS AND APPARATUS THEREOF

This is a division of application Ser. No. 09/696,460 filed Oct. 25, 2000 abandoned and claims the benefit thereof under 35 U.S.C. §120.

BACKGROUND OF THE INVENTION

A. Technical Field

The present invention relates to a column treating process and an apparatus therefor. More particularly, a subject of the present invention is a column treating process by a distillation column and so on, that is utilized when producing various chemical products and comprises: carrying out physical treatment such as isolation of a treating fluid component or chemical treatment such as reaction, of a treating fluid introduced in a column-shaped treating space, namely a treatment column; and taking out a formed desired product from a column top side by methods such as liquefying after evaporating once.

B. Background Art

In production processes for various chemical products, a column treating process by use of column apparatuses such as a distillation column, an absorption column and a stripping column is generally adopted industrially.

In the column treating process, with a liquid or gas treating fluid introducing to a treatment column, a desired physical or chemical treatment is carried out by heating or stirring the treating fluid in the treatment column, or affecting a fluid component supplied separately; a portion of a fluid after the treatment is moved to an upper portion of the column, namely a top column side, recovered by liquefying at the column top and taken out from the column top side. As the result, the mass above treating work can be carried out continuously and stably.

In the column treating process like this, accompanied by carrying out the treatment of the introduced treating liquid, except for a desired product, impurities may be formed by denaturing or polymerizing a component in the treating fluid. The formed impurities like this may stay or accumulate in the treating fluid without taking out as a desired product. In addition, impurities initially included in the treating fluid that is introduced to the treatment column also stay or accumulate in the treatment column. These impurities are usually apt to collect at the column bottom of the treatment column.

The impurities staying and accumulating in the treating fluid cause problems of: lowering heat-transfer characteristics of the treatment column by precipitating the impurities as a solid product and attaching to inner wall of the treatment column; packing various pipings, machines and so on; contaminating a desired product with a portion of the impurities; and lowering quality and capacity of the chemical treatment that carries out a treating solution.

The problem is illustrated by a concrete example. (Meth) acrylic acid and esters thereof are purified by use of a distillation apparatus comprising a distillation column, a heat exchanger and pipings in connection with both.

In this distilling treatment, polymers formed in the distillation column and are attached to inner wall of the distillation column because (meth)acrylic acid and esters thereof are polymerized easily. If the attached polymers accumulate, situations such as stopping the distillation column also arise. It is necessary to remove polymers attached to inner wall by breaking up the distillation column regularly in order to maintain treating quality of the distillation column and to operate stably. Therefore, it takes much labor and productivity is caused to lower greatly.

As a method to solve this problem, a method that comprises introducing oxygen gas from the column bottom for prevention of polymerization in the distillation column is disclosed in JP-B-34606/1977 and JP-B-61015/1982. A method that comprises taking out streamed solution falling in a rectifying column, separating a polymer in the solution, and circulating the polymer into the rectifying column again is disclosed in JP-A-239341/1996.

Neither the above prior art method that comprises introducing oxygen gas nor the above prior art method that comprises separating a polymer from a fallen reflux solution can remove impurities such as a polymer accumulated in a treating solution enough.

Though a problem such as stopping a distillation column or a rectifying column is not caused for a short time operation, polymers are gradually produced and attached to: an drawing out pipe for a column bottom solution, a forwarding pump for a column bottom solution, a pipe that columns such as a reboiler comprise, a heat exchanger and inner portions of a pipe for a long time operation, and it becomes impossible to continue distilling because of causing to block soon. Except for the polymers produced during the treatment, precipitates such as aforementioned impurities contained in the treating solution and denatured products produced during the treatment, can cause the same problem. Further precipitation and polymerization are increased by attaching these polymers and precipitates in the pipes and machines.

In addition, it can be considered to prevent the impurities from intruding into a treatment column by filtrating a treating solution before introducing into the treatment column. However this method is not effective for impurities that are produced in the treatment column. Methods of hindering the impurities from being forwarded into a treating apparatus of the next step or preventing the impurities from attaching to pipes toward the next step can be considered by filtrating the whole of the column bottom drawn solution and thereafter forwarding the solution to the next step. However it is not useful to prevent the impurities from attaching in the treatment column, and it is difficult to effectively filtrate the column bottom drawn solution that contains plenty of impurities.

These prior treating methods cannot prevent solid products from attaching in the pipes and machines enough.

SUMMARY OF THE INVENTION

A. Object of the Invention

An object of the present invention is to provide a column treating method by use of the aforementioned distillation column and so on, which method enables to effectively remove solid impurities such as precipitates and polymers contained or produced in a treating fluid, and to thereby stably operate the column treatment.

B. Disclosure of the Invention

A column treating process, according to the present invention, comprises: introducing a treating fluid in a treatment column, carrying out physical and/or chemical treatment of the treating fluid in the treatment column, taking out a portion of a fluid after the treatment from a column top side, and drawing out a residual fluid that is not taken out from the column top side but is left from a column bottom side. And with advancing the treatment in the treatment column, the process further comprises performing continuously:

- step (a): drawing out the treating fluid from the column bottom side outside the treatment column,
- step (b) of removing solid impurities from the treating fluid drawn out in step (a), and
- step (c) of returning the treating fluid, from which the solid impurities are removed in step (b), to the treatment column.

A column treating apparatus, according to the present invention, which carries out the column treating process and comprises:

- a treatment column, in order to carry out the treatment of the treating fluid in the treatment column,
- an introducing inlet, placed in the treatment column in order to introduce the treating fluid,
- a taking out outlet, placed on the column top side of the treatment column in order to take out a portion of the fluid after the treatment,
- a treating fluid circulating route, placed on the column bottom side of the treatment column in order to draw out the treating fluid in the treatment column outside the treatment column and to return the treating fluid again to the treatment column, and
- an impurities-removing portion, placed in the circulating route in order to remove the solid impurities from the treating fluid.

These and other objects and the advantages of the present invention will be more fully apparent from the following detailed disclosure.

EXPLANATION OF THE SYMBOLS

Figure 1:
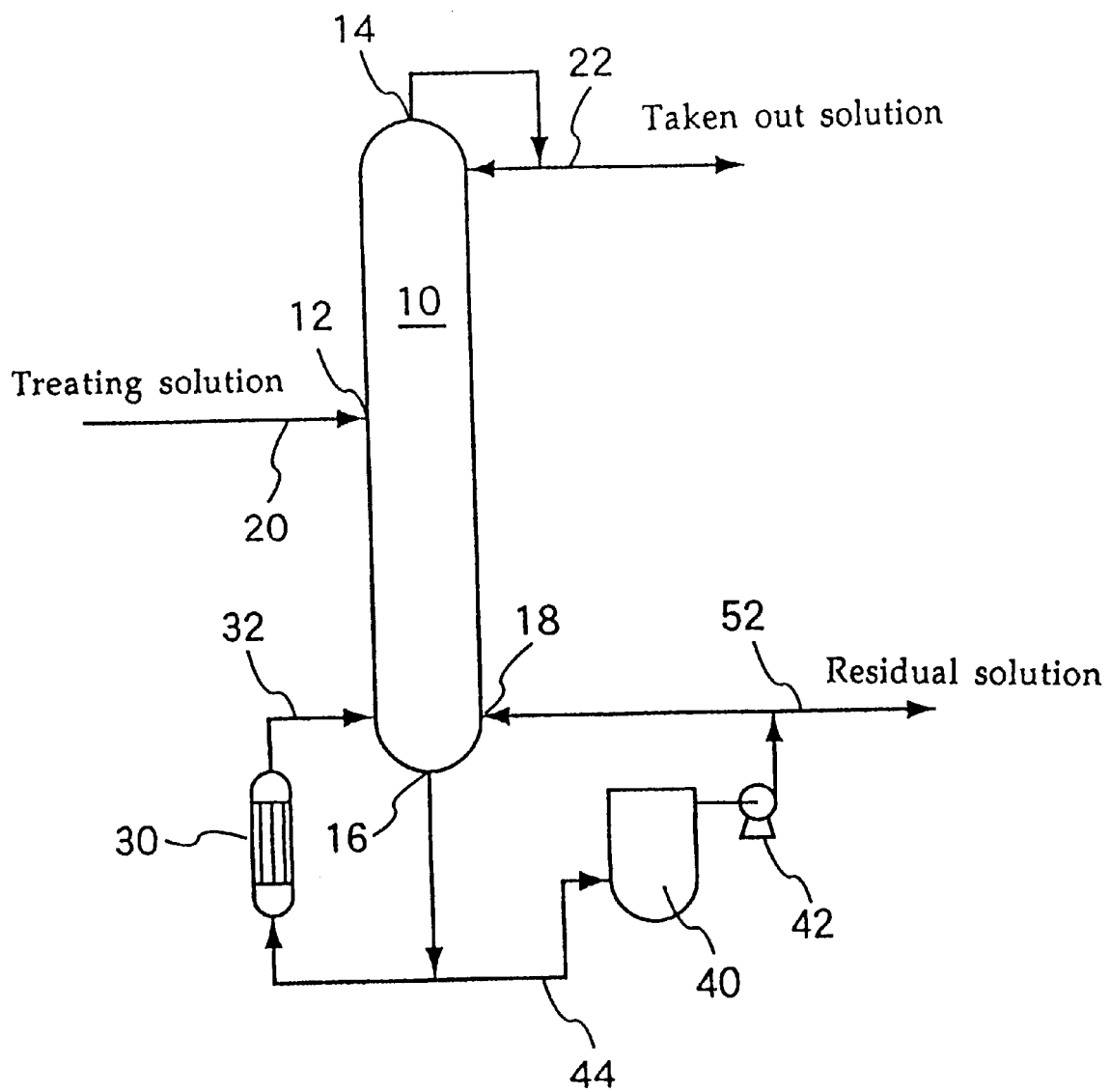
FIG. 1 is a structural view of a treatment apparatus of a mode for carrying out the present invention.

10: Distillation column, 12: Introducing inlet, 16: Drawing out outlet, 14: Taking out outlet, 18: Returning inlet, 20: Introducing pipe, 22: Taking out pipe, 30: Reboiler, 32: Circulating pipe, 40: Strainer, 42: Pump, 44: Circulating pipe, 52: Forwarding pipe

DETAILED DESCRIPTION OF THE INVENTION (Column Treating Process)

A tower-shaped treating apparatus, namely, a treatment column can be used so that physical treating processes such as distillation, absorption, stripping, rectification, separation, extraction, adsorption, collection and other else, or chemical treating processes, or treating processes that the physical and chemical treating processes advance at the same time, can be carried out.

Particularly, the process and the apparatus according to the present invention are preferable to use for a treatment column to carry out physical treatment, and is more preferable to use for a distillation column or a rectifying column among the treatment columns to carry out physical treatment. This reason is that: a treating fluid is frequently exposed to comparatively high temperature in the physical treatments such as distillation, absorption and rectification, and a solid product is easily apt to accumulate in the column, especially at the column bottom side because of polymerizing or burning a treating fluid then. Among these, the distillation column and rectifying column have portions that easily happen to polymerize and to burn, such as a reboiler at the bottom side, and the solid product is apt to accumulate most. These treatment columns can be operated stably by use of the process and the apparatus according to the present invention.

A fundamental form of the treatment column may be the same as an usual treatment column.

A treatment column in which a treating fluid can pass comprises an introducing inlet in order to introduce the treating fluid. The introducing inlet is usually placed in the middle of the treatment column. However the introducing inlet can be placed wherever from the column top side to the column bottom side in compliance with treating conditions of the treatment column. The column bottom side is used as a meaning of: not only the column bottom literally but also including a position lower than the treatment column compared with the below mentioned taking out outlet, even if the position is on the way of a side or middle portion of the treatment column. The introducing inlets can be placed at one portion or plural portions.

The treating fluid is a liquid or a gas. The treating fluid includes a treating component comprising inorganic or organic treating material, a solvent and so on. The treating fluid may include a solid product. One kind of the treating fluid can be introduced, and plural kinds of the treating fluids can be introduced from the same introducing inlet or another introducing inlet into the treatment column. The treating fluid can be introduced into the treatment column continuously or intermittently.

The inner portion of the treatment column is: entirely vacant, comprising a partition or a guide in order to control a stream of the treating fluid, comprising a heat exchange mechanism in order to heat or cool the treating fluid, a stirring mechanism in order to stir the treating fluid, or packed with a solid product to react with the treating fluid or to have some effects on. These inner mechanisms can be placed in combination with the same mechanism structure as that of usual treatment column properly according to difference of the above treatment to treat the treating fluid.

As an equipment attached to the treatment column, a reboiler and so on can be equipped outside the treatment column. The reboiler circulates the treating fluid in the treatment column and controls temperature of the treating fluid.

A taking out outlet in order to take out a portion of obtained fluid as a result of the treatment to the treating fluid, is placed on the column top side of the treatment column. A desired product to take out may be a gas or a liquid. The column top side on which the taking out outlet is placed, not only means the column top position, but also includes a position from a side portion in the neighborhood of the treatment column top to a middle portion of the treatment column and means a position relatively close to the column top compared with the below mentioned drawing out outlet for a residual fluid. Therefore, the column top side can mean a position lower than the just middle position of the entire height of the treatment column. The taking out outlets can be placed at plural portions such as the top and the middle of the treatment column.

A drawing out outlet in order to extract a residual fluid that remains in the treatment column and is not taken out from the above taking out outlet, is placed on the column bottom side of the treatment column. The residual fluid is abandoned as a waste matter or utilized in order to obtain another desired product in the next step. The residual fluid is usually a liquid. The residual fluid is extracted from the treatment column continuously or intermittently. The column bottom side on which the drawing out outlet is placed, means a position relatively close to the column bottom compared with the attached position of the taking out outlet, and does not mean the bottom of the treatment column only.

(Removal of Impurities):

Except for the treatment column, a treating fluid circulating route is placed on the column bottom side of the treatment column in order to draw out the treating fluid in the treatment column outside the treatment column and to return the treating fluid again to the treatment column, and impurities are removed in this circulating route.

The treatment column has a drawing out outlet and a returning inlet for the treating fluid connected with the circulating route. Attached positions of the drawing out outlet and the returning inlet can be properly determined in consideration of an operating condition for a treating procedure of the treatment column. The drawing out outlet is preferably placed at the column bottom. The returning inlet is preferably placed at the column bottom side, and at the column bottom or a side close to the column bottom, and more preferably at the column bottom. The impurities can be removed efficiently by drawing out a treating fluid at the column bottom side where the impurities are apt to accumulate. A treating fluid from which impurities are removed is returned to the treating fluid having the same component ratios at the column bottom side. Therefore, it is difficult to have a bad influence on treating in the treatment column.

The circulating route can comprise a conventional pipe. The circulating route can comprise a pump as a means of flow in order to flow the treating fluid in the circulating rout. The larger the circulation amount of the treating fluid in the circulating route is, the more effectively the impurities can be removed. However, the amount can be determined properly in consideration of amounts and properties of the solid impurities in the treating solution. The amount of the treating solution, usually 0.05 to 100 times weight of residual solution forwarded from the treatment column, preferably 0.1 to 20 times, more preferably 0.2 to 5 times, is circulated in the circulating route in order to remove the impurities.

An impurities-removing portion in order to remove the solid impurities from the treating fluid is placed on the way of the circulating route outside the treatment column. In the impurities-removing portion, the solid impurities are removed from the treating fluid by various chemical or physical means adopted as conventional chemicals production techniques. Among these, it is preferable to use the physical means. The physical means is frequently more excellent in removing effect than the chemical means because the physical means can remove the solid impurities directly. Concretely, a filtration through a strainer, a filter and so on can be adopted. In addition, after introducing the treating fluid into a thin-layer evaporator, a solution drawn out from the thin-layer evaporator is introduced into the strainer and the impurities can be removed. After introducing the fluid into the strainer, a treating fluid drawn out from the strainer can be introduced into the thin-layer evaporator.

Attached positions of the impurities-removing portion is not especially limited if the impurities-removing portion is placed on the way of the circulating route that the treating fluid passes. The circulating route having the impurities-removing portion can be arranged as another route except for the route for drawing out the above residual fluid, or can be shared with the drawing out route and a portion of the route. As this shared form, the circulating route is branched off down stream from the impurities-removing portion, and one branched route can be connected to the returning inlet of the treatment column and the other branched route can be connected to the drawing out route for the residual fluid. Furthermore, a portion of the circulating route for the treating solution to a reboiler placed as an accessory to the treatment column, can be shared with the circulating route of the impurities-removing portion.

Polymers can be prevented from forming by utilizing a polymerization inhibitor when the above treatment is carried out in the treatment column. Examples of the polymerization inhibitor include hydroquinone, methoquinone, phenothiazine, copper salts compounds, manganese salt compound, p-phenylenediamine compounds, N-oxyl compounds and nitroso compounds.

Treatment by use of the treating column can be operated further stably and for a long time by adding molecular oxygen into the treating fluid in addition to the polymerization inhibitor. The molecular oxygen can be supplied at any position of the route that the treating fluid flows, and example thereof include a pipe before introducing into the treatment column, a treatment column bottom or side, machines such as a reboiler placed as an accessory to the treatment column, a pipe, the impurities-removing portion, the pipe thereof, and the route for drawing out the above residual fluid.

The addition amount of the molecular oxygen can be determined properly according to a purpose, but, for a example, it is desirable that the molecular oxygen in the range of 0.1 to 1.0 volume % per vaporized vapor amount of (meth)acrylic acid or ester thereof is added in a distillation column for (meth)acrylic acid and so on.

(Uses)

The present invention is applicable to various column treating processes that use the aforementioned treatment column, for example, is utilized for the below mentioned use preferably.

The present invention is utilized for treatments such as distillation and absorption in a production process for (meth)acrylic acid or (meth)acrylic acid ester. Concretely, if the present invention is applied to purification treatments carried out after producing (meth)acrylic acid and so on, a problem of forming and attaching polymers can be solved.

A compound to be subjected to carry out the above treatment in the treatment column, is not especially limited, but a compound easily to form solid impurities such as polymers is preferably used. Concretely, vinyl compounds, among the vinyl compounds, (meth)acrylic acid and esters thereof to be, especially polymerizable can be preferably used. Examples of the acrylic acid ester as a product to be applied, include methyl acrylate, ethyl acrylate, butyl acrylate, 2-ethylhexyl acrylate, 2-hydroxyethyl acrylate and 2-hydroxypropyl acrylate. Examples of the methacrylic acid ester as a product to be applied, include methyl methacrylate, butyl methacrylate, 2-hydroxyethyl methacrylate and 2-hydroxypropyl methacrylate.

(Effects and Advantages of the Invention):

The column treating process and the apparatus therefor, according to the present invention, enable to prevent impurities from attaching to equipped machines or pipes of a treatment apparatus and to thereby carry out an aimed treatment stably, because solid impurities such as precipitates and polymers produced in a treating solution, which is subjected to physical or chemical treatment in a treatment column, can effectively be removed with an impurities-removing portion as furnished to a circulating route.

DETAILED DESCRIPTION OF THE PREFERRED EMBODIMENTS

A mode for carrying out the invention illustrated in FIG. 1 explains a case applied to distillation treatment of (meth) acrylic acid.

(Meth)acrylic acid is supplied as a treating solution consisting of a mixture with other components. The treating solution is introduced from a introducing pipe (20) to a distillation column (10) through an introducing inlet (12). The introducing inlet (12) is placed at a side of the distillation column (10) around in the middle thereof along a vertical direction.

The treating solution including (meth)acrylic acid is heated in the distillation column (10). A distillate that rises in the column by evaporation, is liquefied at a column top and taken out from a taking out outlet (14) to a taking out pipe (22). The resultant taken out solution includes water, a solvent or (meth)acrylic acid. The taking out pipe (22) has a route branched off on the way and returned to the distillation column (10).

A reboiler (30) is placed below the distillation column (10). The distillation column (10) and the reboiler (30) are connected by a circulating pipe (32) that circulates between both. A treating solution drawn out from a drawing out outlet (16) directly placed at the column bottom of the distillation column (10), is introduced into the reboiler (30) through the circulating pipe (32), heated at the reboiler (30), thereafter returned to around the column bottom of the distillation column (10) through the circulating pipe (32). In this manner, temperature of the treating solution in the distillation column (10) is adjusted within a definite temperature and distillation is operated stably. A treating fluid is spontaneously circulated in the circulating pipe (32) by spontaneous convection currents caused by heating at the reboiler (30).

The circulating pipe (32) branches between the drawing out outlet (16) and the reboiler (30), and is connected to a circulating pipe (44). The circulating pipe (44) is connected to a strainer (40) and a pump (42) successively, and connected to the distillation column (10) at a returning inlet (18) that placed at the column bottom of the distillation column (10).

A portion of the treating solution drawn out from the drawing out outlet (16) of the distillation column (10) is forwarded to the circulating pipe (44) by force, filtrated through the strainer (40), and solid impurities contained in the treating solution are removed, thereafter the resultant solution is returned to the distillation column (10) through the returning inlet (18).

As a result, as to the treating solution in the distillation column (10), the solid impurities are prevented from staying and accumulating, and a problem of attaching the solid impurities to an inner wall of the distillation column (10) and so on is solved. If the solid impurities are not accumulated in the treating solution in the distillation column (10), the solid impurities are not attached to the reboiler (30) and the circulating pipe thereof (32).

In addition, the circulating pipe (44) branches between the pump (42) and the returning inlet (18), and is connected to a forwarding pipe (52). The forwarding pipe (52) is a pipe for forwarding a residual solution treated at the distillation column (10) to a next treating process. A treating solution in which the solid impurities are removed by the above strainer (40) is forwarded as a residual solution. As a result, the solid impurities can be prevented from being attached to the forwarding pipe (52) and forwarding to the next process.

(Line Applied to Production Process for Acrylic Acid)

Figure 2:
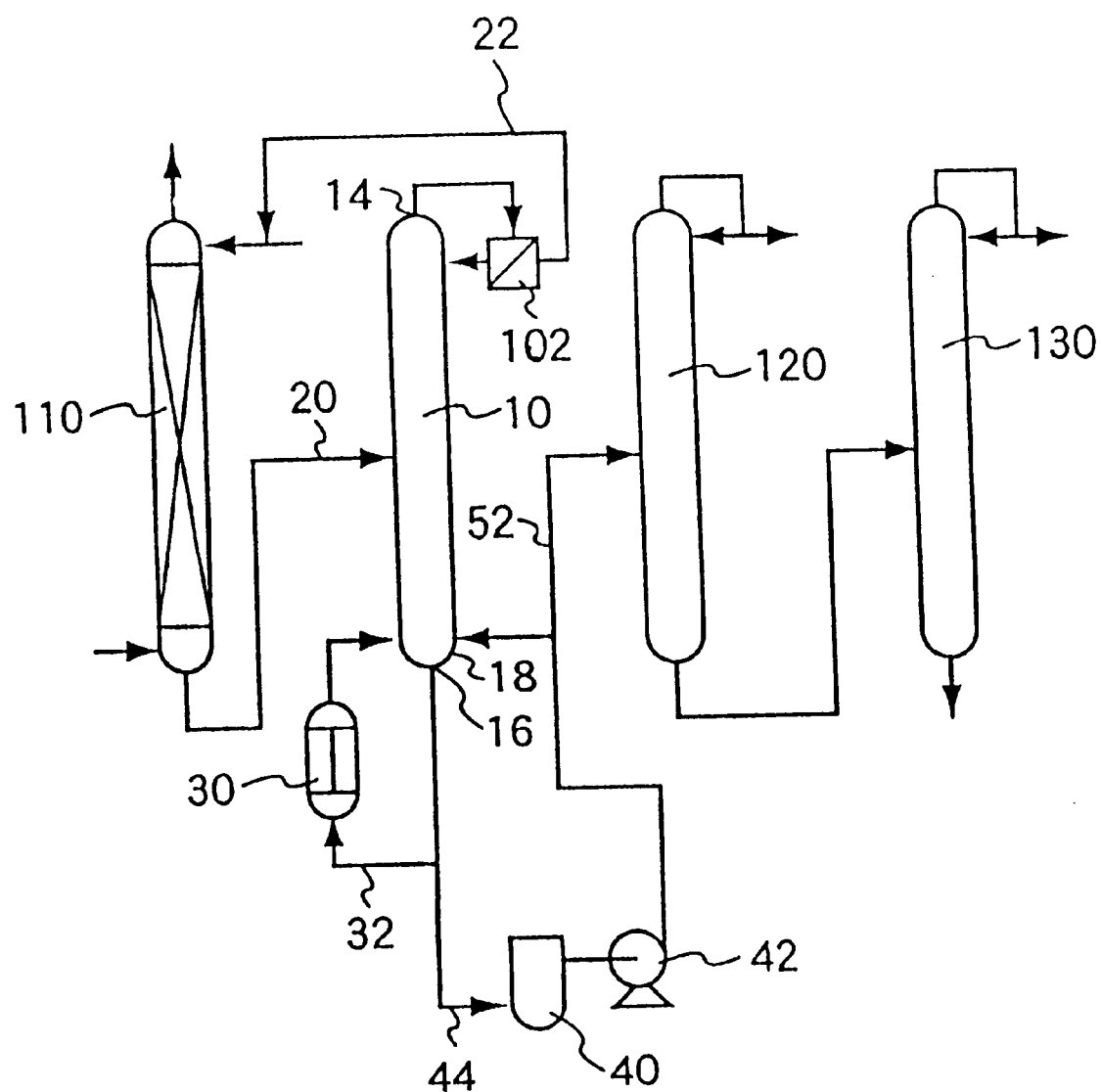
FIG. 2 is a structural view of a treatment apparatus of another mode for carrying out the present invention.

A line applied to a production process for acrylic acid, that includes distilling treatment of (meth)acrylic acid explained in the above mode for carrying out the invention, is illustrated in FIG. 2.

The distillation column (10) illustrated in FIG. 1 is utilized as an azeotropic separation column. The azeotropic separation column (10) and pipings and equipments in the neighborhood of the column is common to that of the distillation column (10) in FIG. 1.

A storing tank (102) is placed on the way of the taking out pipe (22) of the azeotropic separation column (10). The taking out pipe (22) is connected to a column top of an acrylic acid collection column (110), and acrylic acid is captured there.

The introducing pipe (20) of the azeotropic separation column (10) is connected to a column bottom of the acrylic acid collection column (110). The treating solution as a raw material, is introduced into the azeotropic separation column (10) with acrylic acid captured in the acrylic acid collection column (110) through the azeotropic separation column (10).

The forwarding pipe (52) of the azeotropic separation column (10) is connected to a low boiling product separation column (120) and a high boiling product separation column (130) successively. The low boiling product and the high boiling product in the residual solution forwarded from the forwarding pipe (52) are separated through the separation columns (120, 130) respectively.

In the illustrated mode for carrying out the invention, the impurities-removing portion such as the strainer (40) is placed only at the azeotropic separation column (10). However the impurities-removing portion can be placed at other treatment columns such as the collection column (110), the low boiling product separation column (120) and the high boiling product separation column (130).

WORKING EXAMPLES

Hereinafter, the present invention is more specifically illustrated by the following examples of some preferred embodiments in comparison with comparative examples not according to the invention. However, the invention is not limited to the below-mentioned examples.

Example 1

An acrylic acid solution was distilled by use of a distillation apparatus that comprises as shown in FIG. 1.

A distillation column (equipped with 40 pieces of dual flow trays) having 1.8 m column diameter, comprises a taking out outlet and a taking out pipe at a column top. In the middle of the column, the column is equipped with an introducing pipe to which a treating solution as a raw material is supplied and an introducing inlet. Below the column, the column is equipped with a circulating pipe that the treating solution circulates and a strainer on the way of the pipe. In addition, the column is equipped with a vertical shell and tube type reboiler (inner tube diameter: 30 mm, tube length: 4000 mm, and tube number: 310 pieces), and the treating fluid circulates spontaneously and passes in a tube of the reboiler.

A reaction gas included acrylic acid produced by catalytic gas phase oxidation of propylene, and an acrylic acid solution (acrylic acid: 65 weight %, acetic acid: 2 weight %, water: 31 weight % and others: 2 weight %) obtained by absorbing acrylic acid contained in the reaction gas into water, was used as the treating solution. The treating solution was supplied at the twentieth tray of the distillation column at the rate of 6300 kg per hour.

Methyl isobutyl ketone was used as a refluxed solution and supplied to the column top in the rate of 8500 kg per hour.

The distillation column was operated at operating pressure of 150 hPa and at column bottom temperature of 100° C., water and methyl isobutyl ketone were separated from the column top, and crude acrylic acid as a residual solution was recovered from the column bottom at the rate of 5160 kg per hour.

Then, 30 ppm of dibutyl dithiocarbamic acid copper salt and 200 ppm of hydroquinone (each amount is based on vaporized amount of acrylic acid) were used as polymerization inhibitors, and added to the refluxed solution from the column top and dissolved in order to introduce. In addition, 0.3 volume % of molecular oxygen based on vaporized amount of acrylic acid was added from the column bottom of the distillation column.

The crude acrylic acid solution drawn out from the bottom was introduced into the strainer, and the resultant solution from the strainer was circulated to the returning inlet at the rate of 860 kg per hour by use of a column bottom solution forwarding pump. In addition, a portion of the solution from the strainer was forwarded to a forwarding pipe and recovered outside at the rate of 4300 kg per hour.

After the distillation column was operated for 90 days continuously in this operating condition, a stable operating state was obtained all the time. After stopping the operation, it was not detected at all that solid products were attached to a column bottom solution drawing out outlet, the column bottom solution forwarding pump, the circulating pipe and the reboiler, respectively.

Comparative Example 1

An acrylic acid solution was distilled in the same way of Example 1 except that the solution from the strainer was not circulated to a returning inlet but the whole solution was forwarded to the forwarding pipe.

The operation was stopped on the 25th day because shell pressure of the reboiler was detected to rise in operation. As a result after checking, it was detected that solid products were attached to a column bottom solution drawing out outlet, the column bottom solution forwarding pump, the circulating pipe and the reboiler, and especially among 310 pieces of all the tubes of the reboiler, 107 pieces of tubes were blocked with the solid products.

Example 2

Crude butyl acrylate was distilled with a distillation column (equipped with 20 pieces of dual flow trays) having 1.2 m column diameter. The distillation column comprises a refluxed solution supplying pipe at the column top and a treating solution introducing inlet at the column bottom. The column is equipped with a forced-circulating horizontal shell and tube type reboiler (inner tube diameter: 30 mm, tube length: 4000 mm, and tube number: 70 pieces), and a process fluid passes in a tube of the reboiler. In addition, the column is equipped with a circulating route for a treating solution and a strainer.

Crude butyl acrylate (butyl acrylate: 97.5 weight %, butyl butoxy propionate: 1.8 weight %, and others: 0.7 weight %) produced by esterification reaction of acrylic acid and butanol was used as the treating solution. The treating solution was supplied into the column bottom at the rate of 4700 kg per hour. Butyl acrylate distilled from the column top was supplied into the column top at the reflux ratio of 0.3. The distillation column was operated at operating pressure of 70 hPa and at column bottom temperature of 90° C. Purified butyl acrylate not containing high boiling impurities was distilled from the column top at the rate of 4500 kg per hour, and butyl acrylate containing concentrated high boiling impurities was drawn out from the column bottom at the rate of 400 kg per hour. Then, 150 ppm of hydroquinone monomethyl ether was added to the refluxed solution from the column top and dissolved in order to introduce. In addition, 0.3 volume % of molecular oxygen based on vaporized amount of butyl acrylate was added from the column bottom of the distillation column.

A treating solution drawn out from the column bottom of the distillation column forcedly, was caused to pass the strainer with a pump placed at a circulating pipe. A portion of the solution passed the strainer was circulated to the column bottom at the rate of 200 kg per hour, and a portion of the residual solution was forwarded to a forwarding pipe and recovered outside at the rate of 200 kg per hour.

After the distillation column was operated for 60 days continuously in this operating condition, a stable operating state was obtained all the time. After stopping the operation, it was not detected at all that solid products were attached to a column bottom solution drawing out outlet, the column bottom solution forwarding pump, the circulating pipe and the reboiler, respectively.

Comparative Example 2

Crude butyl acrylate was distilled in the same way of Example 2 except that the solution passed the strainer was not returned to a returning inlet but the whole solution was recovered outside.

The operation was stopped on the 21st day because shell pressure of the reboiler was detected to rise in operation. As a result after checking, it was detected that solid products were attached to a column bottom solution drawing out outlet, the column bottom solution forwarding pump, the circulating pipe and the reboiler, and especially among 70 pieces of all the tubes of the reboiler, 22 pieces of tubes were blocked with the solid products.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A distillation process for an easily polymerizable compound in a distillation column, fluid circulating route and filtrating device, wherein the distillation column comprises a lower portion and an upper portion, an inlet for introducing a fluid to the distillation column, and a taking out outlet for taking a portion of the fluid after treatment out from the upper portion of the distillation column, wherein the fluid circulating route is in communication with the lower portion of the distillation column, wherein the fluid circulating route draws fluid from one part of the lower portion of the distillation column and returns said fluid, from which solid impurities have been removed, to another part of the lower portion of the distillation column, and wherein the filtrating device is in the fluid circulating route, wherein the distillation process comprises the steps of:

a) purifying the fluid in the distillation column, wherein the fluid comprises an easily polymerizable compound, wherein the easily polymerizable compound is (meth) acrylic acid or (meth)acrylic acid ester, wherein the fluid that has been purified is taken out from said taking out outlet or is drawn out from said one part of the lower portion of the distillation column;

b) drawing out a fluid portion including solid impurities directly from said one part of the lower portion of the distillation column into the fluid circulating route, wherein the solid impurities comprise polymers formed in the distillation column by a polymerization of the easily polymerizable compound;

c) removing solid impurities, including polymers formed in the distillation column by a polymerization of the easily polymerizable compound, from said fluid portion in the fluid circulating route with the filtrating device;

d) returning said fluid portion, from which said solid impurities have been removed, via the fluid circulating route back to said another part of the lower portion of the distillation column; and e) conducting the steps of purifying, drawing, removing and returning continuously.

2. A distillation process according to claim 1, wherein a branch extends from the circulating route, wherein the branch engages the circulating route between the filtrating device and said another part of the lower portion of the distillation column, and further comprising the step of:

forwarding said fluid portion, from which solid impurities have been removed, into said branch as a residual fluid.

* * * * *